United States Patent [19]

Love

[11] 3,980,639
[45] Sept. 14, 1976

[54] AMOXICILLIN DERIVATIVES

[75] Inventor: Dennis Anthony Love, Redhill, England

[73] Assignee: Beecham Group Limited, Great Britain

[22] Filed: Sept. 8, 1975

[21] Appl. No.: 611,199

[30] Foreign Application Priority Data

Sept. 18, 1974 United Kingdom............... 40661/74

[52] U.S. Cl................................ 260/239.1; 424/271
[51] Int. Cl.² ........................................ C07D 499/68
[58] Field of Search................... 260/239.1; 424/271

[56] References Cited
UNITED STATES PATENTS

| | | | |
|---|---|---|---|
| 3,654,265 | 4/1972 | Essery et al...................... | 260/239.1 |
| 3,741,963 | 6/1973 | Hopewell et al................ | 260/243 C |

FOREIGN PATENTS OR APPLICATIONS

| | | | |
|---|---|---|---|
| 1,380,741 | 1/1975 | United Kingdom............. | 260/239.1 |

Primary Examiner—Gerald A. Schwartz

[57] ABSTRACT

Amoxycillin derivatives, their preparation and injectable compositions containing such derivatives. A preferred composition comprises a mixture of sodium amoxycillin and D-α-carboxyamino-p-hydroxybenzylpenicillin disodium salt in a 1:1 ratio and a pharmaceutically acceptable carrier. Typically, 0.25 g of a mixture according to the invention is dissolved in about 0.5–5 ml of sterile water or saline to form an injectable composition.

2 Claims, No Drawings

AMOXICILLIN DERIVATIVES

This invention relates to derivatives of amoxycillin, to their preparation and to injectable pharmaceutical compositions containing them.

Amoxycillin is the generic name for D-(−)-α-amino-p-hydroxybenzylpenicillin. Amoxycillin is a valuable antibiotic which has a broad antibacterial spectrum and gives high blood levels of the antibiotic after oral administration to a human subject. Whilst the benefits of amoxycillin are manifested to the greatest extent when it is administered by the oral route, it is often desirable to commence an antibiotic course of treatment with parental administration, for example, an unconcious patient may initially be treated parentally and then, when convenient, the mode of administration may be changed to the oral route. However, it is undesirable that such a change should involve a change in the antibiotic itself and accordingly an injectable preparation of amoxycillin is desirable. Hitherto it has proved to be more difficult than expected to prepare a solution of amoxycillin which is sufficiently stable for use in an injectable preparation because aqueous solutions of amoxycillin salts have a tendency to decompose with the consequent appearance of cloud in the injectable solution.

It has now been found that the above-mentioned difficulties may be overcome by the conversion of amoxycillin into its carbamate derivatives.

Accordingly, from one aspect this invention provides compounds of the formula (I):

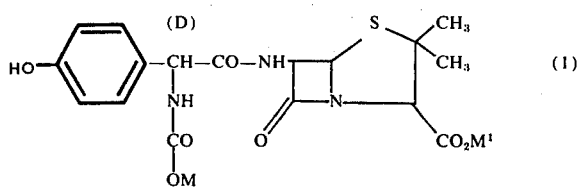

wherein one of M and $M^1$ is a salting ion and the other is a hydrogen ion or both of M and $M^1$ are salting ions, said salting ions being selected from sodium, potassium, magnesium, calcium, ammonium and pharmaceutically acceptable substituted ammonium ions.

More suitably neither M or $M^1$ is hydrogen as in general the dibasic salts are more soluble.

Most suitably the compound of formula (I) is in the form of the mono- or di- sodium or potassium salt.

Preferably the compound of formula (I) is in the form of the di-sodium salt.

The compounds of the formula (I) tend to dissociate in aqueous solution so that they are obtained in admixture with a salt of amoxycillin with cation $M^1$ and a carbonate or bicarbonate salt. However, this does not appear to diminish the effectiveness of the composition.

Accordingly, from a second aspect, this invention provides mixtures of a salt of amoxycillin with a compound of the formula (I).

In such mixtures the ratio of the amoxycillin salt to the compound of the formula (I) will usually be between 2:1 and 1:2 and will frequently be approximately 1:1. This ratio can be determined by n.m.r. spectroscopy and is thought to represent an equilibrium mixture obtained in solution between the amoxycillin salt and the compound of the formula (I).

Compounds of the formula (I) and the mixtures containing compounds of the formula (I) and a salt of amoxycillin may be prepared by the reaction of amoxycillin and a compound of the formula $MHCO_3$, $M_2CO_3$ or $M^1{}_2CO_3$ or mixtures thereof in an aqueous medium. If desired the bicarbonate or carbonate salts may be generated in situ from $CO_2$ and an hydroxide MOH or $M^1OH$.

If desired the solution of amoxycillin may be partly or wholly neutralized before addition of the carbonate or bicarbonate, for example, by using a solution of MOH, $M^1OH$ or the like.

Generally it is preferred to utilize a carbonate in such reactions as this frequently enables somewhat lower temperatures to be used than if the corresponding bicarbonate were utilized, which in turn can lead to less degradation taking place.

It is frequently advantageous to perform the above reaction at a slightly elevated temperature, for example, at 30°–60°C, or more suitably at about 35–50°C.

Most suitably the compound of the formula (I) or the mixtures of of this invention are obtained from solution by freeze-drying or spray drying.

The above process for the production of the compound of the formula (I) or the mixtures of this invention may be considered unusual in that an aqueous solution of a penicillin is warmed in the presence of a base without undue degradation taking place which might have been considered likely under such circumstances. A further unusual feature is that freeze-drying is the preferred method of isolating the compound of the formula (I) or the mixture while more conventional methods such as precipitation using acetone are not satisfactory.

An alternative method of preparation of the compound of formula (I) or the mixtures of this invention is by the removal of a group R from a compound of the formula (II):

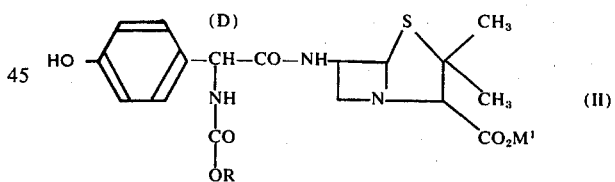

wherein $M^1$ is as defined with respect to formula (I) and R is a group readily cleaved by hydrogenation or hydrolysis.

Suitably R is a benzyl group.

Such a reaction will not be carried out under acid conditions. The desired product is suitably obtained from solution by freeze-drying or by spray drying.

The compounds of the formula (I) may be presented for use as compositions adapted for administration by injection or infusion. Such compositions may be in conventional form, for example, the compound of the formula (I) may be sealed in a sterile ampoule and made up prior to use by dissolution in sterile water or the like.

Such compositions preferably comprise a salt of amoxycillin and a compound of the formula (I) in the approximate ratio of 1:1 together with a pharmaceutically acceptable carrier.

A preferred composition of this invention comprises sodium amoxycillin and D-α-carboxyamino-p-hydroxybenzylpenicillin disodium salt in the approximate ratio of 1:1 together with a pharmaceutically acceptable carrier.

Generally 0.25 g. of the mixtures of this invention may be dissolved in about 0.5–5 ml. of sterile water or saline. A conventional volume for such injectable compositions is 1.5 to 2.5 ml.

Normally the compositions of this invention will contain 100-1500 mg. of antibiotic, for example, 125, 250, 500 or 1000 mg.

Surprisingly, it has been found that the compositions of this invention are better tolerated on administration than compositions containing a mixture of amoxycillin and an excess of carbonate sufficient to dissolve the amoxycillin. This may be because when dissolved in water the compounds of this invention have a pH which is lower than either the aforementioned mixture or the corresponding salt of amoxycillin. This surprising effect is believed to be advantageous.

The following Examples illustrate the invention.

EXAMPLE 1

D-α-Carboxyamino-p-hydroxybenzylpenicillin - Disodium Salt

Amoxycillin trihydrate (4.2 g., 10 m.mole) was suspended in a solution of sodium bicarbonate (1.7 g., 20 m.mole) in water (100 ml). The stirred suspension was gently heated to 50° when after several minutes a clear solution was obtained. The solution was cooled and freeze-dried to a bulky, crisp, white solid (4.8 g.), purity 79% (hydroxylamine assay) containing 7% water (Kark Fischer). On resolution in water (0.25 g. in 2.0 ml., a concentration commonly used for injection), a pH of 8.4 was obtained.

An n.m.r. spectrum of the product in $D_2O$ solution was compared with a spectrum of sodium amoxycillin =

| Spectrum of product | Spectrum of sodium amoxycillin | Assignment |
|---|---|---|
| centred on 1.5 ppm, m, 6H | 1.4 to 1.6 ppm, d, 6H | 2-gemdimethyl protons |
| 4.25, s, 0.5H) 4.3, s, 0.5H) | 4.25, s, 1H | 3-C proton |
| 4.7, s, 0.5H) 5.15, s, 0.5H) | 4.6, s, 1H | a-C proton |
| 5.5, broad s, 2H | 5.4–5.6, broad s, 2H | 5 and 6-C protons |
| 6.8 to 7.4, AA'BB'm, 4H | 6.8–7.4, AA'BB'm, 4H | Aromatic protons |

EXAMPLE 2

D-α-Carboxyamino-p-hydroxybenzylpenicillin — Disodium Salt

Amoxycillin trihydrate (4.2 g., 10 m.mole) was suspended in a solution of sodium bicarbonate (1.7 g., 20 m.mole) in water (100 ml.). The suspension was stirred at room temperature for 5 hours, when solid dissolved to give a pale-yellow solution. This was freeze-dried to give a product (4.7 g.), purity 71% (hydroxylamine assay) showing the same n.m.r. spectrum as that of the similar product from Example 1. On resolution in water (0.25 g. in 2.0 ml.), a pH of 8.5 was obtained.

EXAMPLE 3

D-α-Carboxyamino-p-hydroxybenzylpenicillin — Monosodium Salt

Amoxycillin trihydrate (4.2 g., 10 m.mole) was suspended in a solution of anhydrous sodium carbonate (0.53 g., 5 m.mole) and water (100 ml.). The stirred suspension was gently heated over 20 minutes to 40° when a clear solution was obtained. This was cooled and freeze-dried to give a product (4.7 g.), purity 87% (hydroxylamine assay) showing substantially the same n.m.r. spectrum as that of the disodium salt in Example 1. On resolution in water (0.25 g. in 2.0 ml.) a pH of 8.5 was obtained.

EXAMPLE 4

D-α-Carboxyamino-p-hydroxybenzylpenicillin — Disodium Salt

Amoxycillin trihydrate (4.2 g., 10 m.mole) was suspended in water (100 ml.) and sodium hydroxide solution (5.0 ml. of a 2N solution 10 m.mole) added dropwise with stirring when a clear solution was obtained at pH 9.1. Sodium bicarbonate (0.84 g., 10 m.mole) was added and the solution heated at 50° for 20 minutes. The solution was cooled and freeze-dried to give a product (4.6 g.), purity 81% (hydroxylamine assay), containing 10% water (Karl Fischer). An n.m.r. spectrum was the same as that of the similar product from Example 1. On resolution in water (0.25 g. in 2.0 ml), a pH of 8.6 was obtained.

EXAMPLE 5

D-α-Carboxyamino-p-hydroxybenzylpenicillin — Diammonium Salt

Amoxycillin trihydrate (10 m.mole) was suspended in a solution of ammonium bicarbonate (20 m.mole) in water (100 ml.). The stirred suspension was gently heated to 45° for 20 minutes when a clear solution was obtained. The solution was cooled and freeze-dried to a bulky crisp, white solid (4.8 g.), purity 93% (hydroxylamine assay), containing 9% water (Karl Fischer). On resolution in water (0.25 g. in 5 ml.), a pH of between 6 and 7 was obtained.

EXAMPLE 6

D-α-Carboxyamino-p-hydroxybenzylpenicillin — Calcium Salt

Amoxycillin trihydrate (10 m.mole) and calcium carbonate (10 m.mole) was suspended in water (100 ml.). The stirred suspension was warmed to 45° and carbon dioxide bubbled through for 30 minutes. The insoluble material that remained (3.0 g.) was removed by filtration and the filtrate freeze-dried to a bulky, crisp, white solid (2.4 g.), of good purity.

EXAMPLE 7

D-α-Carboxyamino-p-hydroxybenzylpenicillin — Dipotassium Salt

The title compound was prepared by a method exactly analogous to that of Example 1.

EXAMPLE 8

D-α-Carboxyamino-p-hydroxybenzylpenicillin - Disodium Salt

Amoxycillin trihydrate (105 g., 250 m.mole) was suspended in a solution of anhydrous sodium carbonate (26.5 g., 250 m.mole) in water (2200 ml.) which had been preheated to 45°. The mixture was stirred and the temperature raised to 50° when a clear solution was soon obtained. This was fed immediately into a standard commercial spraydrying apparatus to give a dense off-white powder, purity 89% (hydroxylamine assay) containing 6% water (Karl Fischer). The n.m.r. spectrum of the product was found to be substantially similar to that described in Example 1. On resolution in water (0.25 g. in 2.0 ml.) a stable solution of pH 8.9 was obtained.

EXAMPLE 9

D-α-Carboxyamino-p-hydroxybenzylpenicillin — Sodium/Half Calcium Salt

Sodium D-α-benzyloxycarbonylamino-p-hydroxybenzylpenicillin (1.6 g., 3.0 m.mole) was dissolved in water (5.0 ml.) and the solution added to a suspension of 5% pallidised calcium carbonate (4.0 g.) in water (15ml.) which had been prehydrogenated. The mixture was hydrogenated with vigorous shaking at 20° for 2 hours under a slight pressure of hydrogen gas. The catalyst was removed by filtration and the filtrate freeze-dried. The n.m.r. spectrum of the product was found to be substantially similar to that described in Example 1.

EXAMPLE 10

D-α-Carboxyamino-p-hydroxybenzylpenicillin — Bistriethylamine Salt

Amoxycillin trihydrate (4.2 g., 10 m.mole) was suspended in water (100 ml.) and heated to 45° while bubbling through gaseous carbon dioxide. Triethylamine was added dropwise to the stirred suspension so that the pH did not rise above 7.0 and the temperature raised slowly to 50° when the penicillin dissolved. The rest of the triethylamine (to 2.8 ml., 20 m.mole) was then added and the solution immediately cooled and freeze-dried. The product (5.7 g.) had a purity of 60% (hydroxylamine assay) contained 1% water (Karl Fischer) and had an n.m.r. spectrum that resembled that described in Example 1 with additional signals from the triethylamine.

EXAMPLE 11

D-α-Carboxyamino-p-hydroxybenzylpenicillin — Magnesium Salt

Amoxycillin trihydrate (4.2 g., 10 m.mole) and light magnesium carbonate (0.91 g., 2.5 m.mole, 1 equivalent Mg) were suspended in water (100 ml.) which had been preheated to 60°. Gaseous carbon dioxide was bubbled through the stirred suspension for 15 minutes when most of the solid dissolved. The insoluble material was removed by filtration and the filtrate cooled and freeze-dried. The off-white solid prepared had a purity of 86% (hydroxylamine assay) and its n.m.r. spectrum resembled that of the product for Example 1. On resolution in water (0.25 g. in 2.0 ml.) a stable solution of pH 8.2 was obtained.

What is claimed:

1. A compound of the formula:

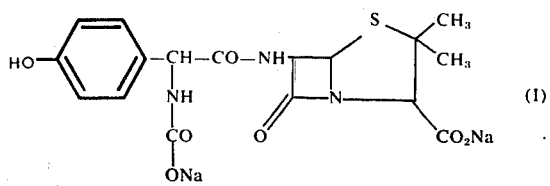

2. A pharmaceutical composition comprising an antibacterially effective amount of the compound of claim 1 together with a pharmaceutically acceptable carrier.

* * * * *